United States Patent
Crowley et al.

(10) Patent No.: US 8,193,361 B2
(45) Date of Patent: *Jun. 5, 2012

(54) I-ALKYNYL 2-ARYLOXYALKYLAMIDES AND THEIR USE AS FUNGICIDES

(75) Inventors: Patrick Jelf Crowley, Bracknel (GB); Roger Salmon, Bracknell (GB); Ewan James Turner Chrystal, Bracknell (GB); Olivia Anabelle Sageot, Bracknell (GB); Laura Quaranta, Basel (CH); Hans-Georg Brunner, Basel (CH); Renaud Beaudegnies, Basel (CH); Fredrik Cederbaum, Basel (CH); Fiona Murphy Kessabi, Basel (CH)

(73) Assignees: Syngenta Limited, Guildford, Surrey (GB); Syngenta Crop Protection LLC, Greensboro, NC (US)

( * ) Notice: Subject to any disclaimer, the term of this patent is extended or adjusted under 35 U.S.C. 154(b) by 844 days.

This patent is subject to a terminal disclaimer.

(21) Appl. No.: 11/720,200

(22) PCT Filed: Nov. 29, 2005

(86) PCT No.: PCT/EP2005/012734
§ 371 (c)(1),
(2), (4) Date: May 25, 2007

(87) PCT Pub. No.: WO2006/058699
PCT Pub. Date: Jun. 8, 2006

(65) Prior Publication Data
US 2008/0096917 A1  Apr. 24, 2008

(30) Foreign Application Priority Data
Dec. 1, 2004 (GB) .................................. 0426372.9

(51) Int. Cl.
*C07D 215/38* (2006.01)
(52) U.S. Cl. ....................................... 546/159; 546/163
(58) Field of Classification Search .................. 546/159, 546/163
See application file for complete search history.

(56) References Cited

U.S. PATENT DOCUMENTS

| | | | |
|---|---|---|---|
| 7,371,764 B2 * | 5/2008 | Crowley et al. | 514/311 |
| 2007/0042996 A1 * | 2/2007 | Crowley et al. | 514/63 |
| 2008/0171767 A1 * | 7/2008 | Salmon et al. | 514/312 |

FOREIGN PATENT DOCUMENTS

| | | | |
|---|---|---|---|
| WO | 2004047538 | * | 6/2004 |
| WO | 2004048316 | | 6/2004 |
| WO | 2004108663 | | 12/2004 |

OTHER PUBLICATIONS

CA142:55899, abstract only of WO 2004108663, 2004.*

* cited by examiner

*Primary Examiner* — D M Seaman
(74) *Attorney, Agent, or Firm* — Kody Jones

(57) ABSTRACT

Compounds of the formula wherein the substituents are as defined in the claims, are useful as fungicides.

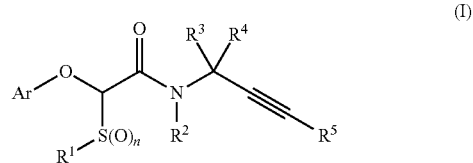

(I)

10 Claims, No Drawings

1-ALKYNYL 2-ARYLOXYALKYLAMIDES AND THEIR USE AS FUNGICIDES

This application is a 371 of International Application No. PCT/EP2005/012734 filed Nov. 29, 2005, which claims priority to GB 0426372.9 filed Dec. 1, 2004, the contents of which are incorporated herein by reference.

This invention relates to novel N-alkynyl-2-alkylthio-2-(substituted aryloxy and heteroaryloxy)alkylamides and to their sulphinyl and sulphonyl derivatives. It also relates to processes for preparing them, to compositions containing them and to methods of using them to combat fungi, especially fungal infections of plants.

Certain pyridyloxy(thio)alkanoic and heteroaryloxy(thio) alkanoic acid amide derivatives and their use as agricultural and horticultural bactericides are disclosed in WO 99/33810 and JP 2001-89453. Certain substituted phenoxybutyramides and their use as mildewicides are described in EP 0,001,721. Certain phenoxy alkanoic acid amides and their use as fungicides are described in WO 04/047537, WO 04/048316 and WO 04/048315. Certain phenoxy and heteroaryloxy alkoxy acetamide derivatives and their use as fungicides are disclosed in WO 04/052100 and WO 04/047538. The use of certain substituted 2-alkylsulphonyl-2-phenoxyalkylanilides as photographic materials is disclosed in JP 61,86702 and in U.S. Pat. No. 4,286,053.

The present invention is concerned with the provision of particular N-alkynyl-2-alkylthio-2-(substituted aryloxy and heteroaryloxy)alkylamides and their sulphinyl and sulphonyl derivatives for use mainly as plant fungicides.

Thus according to the present invention there is provided a compound of the general formula (1):

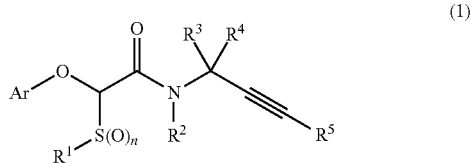

(1)

wherein Ar is a group of the formula (A):

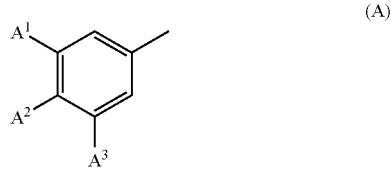

(A)

wherein $A^1$ is aryl (e.g. phenyl), aryloxy (e.g. phenoxy), aryl $(C_{1-6})$alkyl (e.g. benzyl), aryl$(C_{1-6})$alkoxy (e.g. benzyloxy), heteroaryl (e.g. pyridyl), heteroaryloxy (e.g. pyridyloxy), heteroaryl$(C_{1-6})$allyl (e.g. pyridylmethyl) or heteroaryl$(C_{1-6})$alkoxy (e.g. pyridylmethoxy) in which the aryl or heteroaryl moiety is optionally substituted with one, two or three substituents independently selected from halo, cyano, hydroxy, $C_{1-4}$ alkyl, $C_{1-4}$ alkoxy and $C_{1-4}$ alkylthio, and $A^2$ and $A^3$ are independently H, halo (e.g. fluoro, chloro, bromo, iodo), cyano, nitro, $C_{1-6}$ alkyl (e.g. methyl), halo $(C_{1-6})$alkyl (e.g. trifluoromethyl), $C_{3-6}$ cycloalkyl, $C_{3-6}$ cycloalkyl$(C_{1-4})$alkyl, $C_{2-6}$ alkenyl (e.g. allyl), halo$(C_{2-6})$ alkenyl, $C_{2-6}$ alkynyl (e.g. propargyl), halo$(C_{2-6})$alkynyl, $C_{1-6}$ alkoxy (e.g. methoxy), halo$(C_{1-6})$alkoxy (e.g. trifluoro-methoxy), $C_{2-6}$ alkenyloxy (e.g. allyloxy), halo$(C_{2-6})$alkenyloxy, $C_{2-6}$ alkynyloxy (e.g. propargyloxy), halo$(C_{2-6})$alkynyloxy, aryl (e.g. phenyl), aryloxy (e.g. phenoxy), aryl-$(C_{1-6})$alkyl (e.g. benzyl) or aryl$(C_{1-6})$ alkoxy (e.g. benzyloxy), heteroaryl (e.g. pyridyl), heteroaryloxy (e.g. pyridyloxy), heteroaryl$(C_{1-6})$alkyl (e.g. pyridylmethyl) or heteroaryl$(C_{1-6})$alkoxy (e.g. pyridylmethoxy), —$SF_5$, —$S(O)_p(C_{1-4})$alkyl wherein p is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^pR^q$, —$COR^p$, —$CO_2R^p$, —$CR^p$=$NR^q$, —$NR^pR^q$, —$NR^pCOR^q$, —$NR^pCO_2R^q$, —$SO_2NR^pR^q$ or —$NR^pSO_2R^o$ where $R^o$ is $C_{1-4}$ alkyl optionally substituted with halogen and $R^p$ and $R^q$ are independently H or $C_{1-4}$ alkyl optionally substituted with halogen (e.g. —$NHCOCF_3$ or —$N(CH_3)_2$), or, in the case of —$CONR^pR^q$ or —$SO_2NR^pR^q$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted; or $A^1$ and $A^2$ form a 5-membered saturated or unsaturated ring or a 6-, 7- or 8-membered saturated ring optionally substituted with halo (e.g. fluoro), $C_{1-6}$ alkyl (e.g. methyl), $C_{1-6}$ alkoxy (e.g. methoxy), oxo, thioxo, aryl (e.g. phenyl), aryloxy (e.g. phenoxy), aryl-$(C_{1-6})$alkyl (e.g. benzyl), aryl$(C_{1-6})$alkoxy (e.g. benzyloxy), heteroaryl (e.g. pyridyl), heteroaryloxy (e.g. pyridyloxy), heteroaryl$(C_{1-6})$ alkyl (e.g. pyridylmethyl) or heteroaryl -$(C_{1-6})$alkoxy (e.g. pyridylmethoxy), wherein if the ring is a 5-membered saturated ring optionally one or two of the carbon atoms are replaced independently with an O, S or N atom (e.g. indanyl, 1,3-benzodioxolyl, 1,3-benzoxathiolyl, 1,3-benzodithiolyl), or if the ring is a 5-membered unsaturated ring optionally one carbon atom is replaced with an O or S atom (e.g. benzofuranyl, benzothienyl) and the unsaturated 5 membered ring is optionally fused with a benzene or a pyridine ring (e.g. 9H-fluorenyl, dibenzofuranyl, dibenzothienyl, indenopyridyl, benzofuropyridyl, benzothienopyridyl), which can be optionally substituted with halo or $C_{1-4}$ alkyl, or the ring is a 6-, 7- or 8-membered unsaturated ring (e.g. 1,2,3,4-tetrahydronaphthyl), and $A^3$ is H, halo (e.g. fluoro, chloro, bromo, iodo), cyano, nitro, $C_{1-6}$ alkyl (e.g. methyl), halo$(C_{1-6})$alkyl (e.g. trifluoromethyl), $C_{3-6}$ cycloalkyl, $C_{3-6}$ cycloalkyl$(C_{1-4})$alkyl, $C_{2-6}$ alkenyl (e.g. allyl), halo$(C_{2-6})$ alkenyl, $C_{2-6}$ alkynyl (e.g. propargyl), halo$(C_{2-6})$alkynyl, $C_{1-6}$ alkoxy (e.g. methoxy), halo$(C_{1-6})$alkoxy (e.g. trifluoromethoxy), $C_{2-6}$ alkenyloxy (e.g. allyloxy), halo$(C_{2-6})$ alkenyloxy, $C_{2-6}$ alkynyloxy (e.g. propargyloxy), halo$(C_{2-6})$-alkynyloxy, aryl (e.g. phenyl), aryloxy (e.g. phenoxy), aryl$(C_{1-6})$alkyl (e.g. benzyl), aryl-$(C_{1-6})$alkoxy (e.g. benzyloxy), heteroaryl (e.g. pyridyl), heteroaryloxy (e.g. pyridyloxy), heteroaryl$(C_{1-6})$alkyl (e.g. pyridylmethyl), heteroaryl$(C_{1-6})$alkoxy (e.g. pyridylmethoxy), —$SF_5$, —$S(O)_p(C_{1-4})$alkyl wherein p is 0, 1 or 2 and the alkyl group is optionally substituted with halo (particularly fluoro, e.g. trifluoromethylsulphonyl), —$OSO_2(C_{1-4})$alkyl where the alkyl group is optionally substituted with halo (particularly fluoro, e.g. trifluoromethylsulphonyloxy), —$CONR^pR^q$, —$COR^p$, —$CO_2R^p$, —$CR^p$=$NR^q$, —$NR^pR^q$, —$NR^pCOR^q$, —$NR^pCO_2R^q$, —$SO_2NR^pR^q$ or —$NR^pSO_2R^o$ where $R^o$ is $C_{1-4}$ alkyl optionally substituted with halogen and $R^p$ and $R^q$ are independently H or $C_{1-4}$ alkyl optionally substituted with halogen (e.g. —NH-COCF$_3$ or —N(CH$_3$)$_2$), or, in the case of —CONR$^p$R$^q$ or —SO$_2$N$^p$R$^q$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted; or Ar is a group of the formula (B1) or (B2):

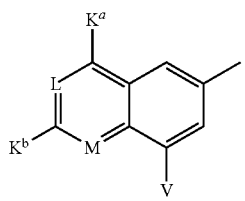

(B1)

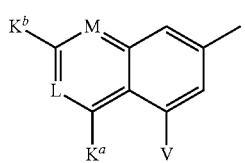

(B2)

wherein L and M are both CQ, or L is N or N-oxide and M is CQ, or L is CQ and M is N or N-oxide;

K$^a$ and K$^b$ are independently H or F;

V is H, halo (e.g. fluoro, chloro, bromo, iodo), cyano, nitro, C$_{1-6}$ alkyl optionally substituted with halo or C$_{1-4}$ alkoxy, C$_{3-6}$ cycloalkyl optionally substituted with halo or C$_{1-4}$ alkoxy, C$_{3-6}$ cycloalkyl(C$_{1-4}$)alkyl optionally substituted with halo or C$_{1-4}$ alkoxy, C$_{2-4}$ alkenyl optionally substituted with halo, C$_{2-4}$ alkynyl optionally substituted with halo, C$_{1-6}$ alkoxy optionally substituted with halo or C$_{1-4}$ alkoxy, C$_{2-4}$ alkenyloxy optionally substituted with halo (e.g. allyloxy), C$_{2-4}$ alkynyloxy optionally substituted with halo (e.g. propargyloxy), aryl (e.g. phenyl), aryloxy (e.g. phenoxy), aryl(C$_{1-6}$)alkyl (e.g. benzyl), aryl(C$_{1-6}$)alkoxy (e.g. benzyloxy), heteroaryl (e.g. pyridyl), heteroaryloxy (e.g. pyridyloxy), heteroaryl(C$_{1-6}$)alkyl (e.g. pyridylmethyl), heteroaryl(C$_{1-6}$)alkoxy (e.g. pyridylmethoxy), —SF$_5$, —S(O)$_p$(C$_{1-4}$)alkyl wherein p is 0, 1 or 2 and the alkyl group is optionally substituted with halo (particularly fluoro, e.g. trifluoromethylsulphonyl), —OSO$_2$(C$_{1-4}$)alkyl where the alkyl group is optionally substituted with halo (particularly fluoro, e.g. trifluoromethylsulphonyloxy), —CONR$^p$R$^q$, —COR$^p$, —CO$_2$R$^p$, —CR$^p$=NR$^q$, —NR$^p$R$^q$, —NR$^p$COR$^q$, —NR$^p$CO$_2$R$^q$, —SO$_2$NR$^p$R$^q$ or —NR$^p$SO$_2$R$^o$ where R$^o$ is C$_{1-4}$ alkyl optionally substituted with halogen and R$^p$ and R$^q$ are independently H or C$_{1-4}$ alkyl optionally substituted with halogen (e.g. —NH-COCF$_3$ or —N(CH$_3$)$_2$), or, in the case of —CONR$^p$R$^q$ or —SO$_2$NR$^p$R$^q$, may join to form a 5- or 6-membered ring containing a single nitrogen atom, a single sulphur atom, saturated carbon ators and optionally a single oxygen atom; wherein any of the foregoing alkyl, cycloalkyl, alkenyl, alkynyl, aryl or heteroaryl groups or moieties are optionally substituted;

Q is aryl (e.g. phenyl), aryloxy (e.g. phenoxy), aryl(C$_{1-6}$)alkyl (e.g. benzyl), aryl(C$_{1-6}$)-alkoxy (e.g. benzyloxy), heteroaryl (e.g. pyridyl), heteroaryloxy (e.g. pyridyloxy), heteroaryl(C$_{1-6}$)alkyl (e.g. pyridylmethyl) or heteroaryl(C$_{1-6}$) alkoxy (e.g. pyridyloxy) in which the aryl or heteroaryl moiety is optionally substituted with one, two or three substituents independently selected from halo, cyano, C$_{1-4}$ alkyl, C$_{1-4}$ alkoxy and C$_{1-4}$ alkylthio;

R$^1$ is C$_{1-4}$ alkyl (e.g. methyl, ethyl), halo(C$_{1-4}$)alkyl (e.g. CF$_3$, CF$_2$H, CF$_2$Cl, CH$_2$CH$_2$F) or C$_{3-4}$ cycloalkyl;

R$^2$ is H, C$_{1-4}$ alkyl, C$_{1-4}$ alkoxymethyl or benzyloxymethyl in which the phenyl ring of the benzyl moiety is optionally substituted with one, two or three C$_{1-4}$ alkoxy groups;

R$^3$ and R$^4$ are independently H, C$_{1-6}$ alkyl, C$_{2-6}$ alkenyl or C$_{2-6}$ alkynyl optionally substituted with halo, C$_{1-4}$ alkoxy, cyano or —S(O)$_m$(C$_{1-4}$)alkyl wherein m is 0, 1 or 2 and the C$_{1-4}$ alkyl group is optionally substituted with halo (particularly fluoro, e.g. trifluoro-methylsulphonyl), provided that both are not H, or R$^3$ and R$^4$ join with the carbon atom to which they are attached to form a 3 or 4 membered carbocyclic ring optionally containing one O, S or N atom and optionally substituted with halo, C$_{1-4}$ alkyl, C$_{1-4}$ alkoxy or cyano;

R$^5$ is H, C$_{1-8}$ alkyl, C$_{3-6}$ cycloalkyl or C$_{3-6}$ cycloalkyl(C$_{1-4}$)alkyl in which the alkyl or cycloalkyl group is optionally substituted with halo, hydroxy, C$_{1-6}$ alkoxy, C$_{1-3}$ alkoxy-(C$_{1-3}$)alkoxy, cyano, C$_{1-4}$ alkylcarbonyl, C$_{1-4}$ alkoxycarbonyl, arylcarbonyl, heteroaryl-carbonyl, C$_{1-4}$ alkylcarbonyloxy, aminocarbonyloxy or mono- or di(C$_{1-4}$) alkyl-aminocarbonyloxy, tri(C$_{1-4}$)alkylsilyloxy, —S(O)$_r$(C$_{1-6}$)alkyl where r is 0, 1 or 2, or R$^5$ is optionally substituted aryl (e.g. phenyl), optionally substituted aryl(C$_{1-4}$) alkyl (e.g. benzyl), optionally substituted aryloxy(C$_{1-4}$) alkyl (e.g. phenoxymethyl), optionally substituted aryl(C$_{1-4}$)alkoxy(C$_{1-4}$)alkyl (e.g. benzyloxymethyl), optionally substituted heteroaryl (e.g. pyridyl, thienyl, pyrazolyl, imidazolyl, triazolyl), optionally substituted heteroaryl(C$_{1-4}$)alkyl (e.g. pyridylmethyl, phthalimidoethyl), optionally substituted heteroaryloxy(C$_{1-4}$)alkyl (e.g. thienyloxymethyl) or optionally substituted heteroaryl -(C$_{1-4}$)alkoxy(C$_{1-4}$)alkyl (e.g. thienylmethoxymethyl), in which the optionally substituted aryl and heteroaryl rings or moieties of the R$_5$ values are optionally substituted with one, two or three substituents independently selected from halo (e.g. fluoro, chloro, bromo, iodo), cyano, nitro, C$_{1-4}$ alkyl (e.g. methyl), halo(C$_{1-6}$)-alkyl (e.g. trifluoromethyl), C$_{3-6}$ cycloalkyl, C$_{3-6}$ cycloalkyl(C$_{1-4}$)alkyl, C$_{2-6}$ alkenyl (e.g. allyl), halo(C$_{2-6}$)alkenyl, C$_{2-6}$ alkynyl (e.g. propargyl), halo(C$_{2-6}$)alkynyl, C$_{1-6}$ alkoxy (e.g. methoxy), halo(C$_{1-6}$)alkoxy (e.g. trifluoromethoxy), C$_{2-6}$ alkenyloxy (e.g. allyloxy), halo-(C$_{2-6}$)alkenyloxy, C$_{2-6}$ alkynyloxy (e.g. propargyloxy), halo(C$_{2-6}$)alkynyloxy, aryl (e.g. phenyl), aryloxy (e.g. phenoxy), aryl(C$_{1-6}$)alkyl (e.g. benzyl), aryl(C$_{1-6}$)alkoxy (e.g. benzyloxy), heteroaryl (e.g. pyridyl), heteroaryloxy (e.g. pyridyloxy), heteroaryl(C$_{1-6}$) -alkyl (e.g. pyridylmethyl), heteroaryl(C$_{1-6}$)alkoxy (e.g. pyridylmethoxy), —SF$_5$, —S(O)$_r$(C$_{1-4}$)alkyl wherein r is 0, 1 or 2 and the alkyl is optionally substituted with halo (particularly fluoro, e.g. trifluoromethylsulphonyl), —OSO$_2$(C$_{1-4}$) alkyl where the alkyl group is optionally substituted with halo (particularly fluoro, e.g. trifluoro -methylsulphonyloxy), —CONR$^s$R$^t$, —COR$^s$, —CO$_2$R$^s$, —CR$^s$=NR$^t$, —NR$^s$R$^t$, —NR$^s$COR$^t$, —NR$^s$CO$_2$R$^t$, —SO$_2$NR$^s$R$^t$ or —NR$^s$SO$_2$R$^r$ where R$^r$ is C$_{1-6}$ alkyl optionally substituted with halogen and R$^s$ and R$^t$ are independently H or C$_{1-6}$ alkyl optionally substituted with halogen (e.g. —NH-COCF$_3$ or —N(CH$_3$)$_2$), or, in the case of —CONR$^s$R$^t$ or —SO$_2$NR$^s$R$^t$, may join to form a 5- or 6-membered ring containing a single nitrogen atom, a single sulphur atom, saturated carbon atoms and optionally a single oxygen atom; wherein any of the foregoing alkyl, cycloalkyl, alkenyl, alkynyl, aryl or heteroaryl groups or moieties are optionally substituted; and n is 0, 1 or 2.

For the avoidance of doubt, the unattached single bond shown in the groups of formulae (A), (B1) and (B2) indicates the point of attachment of the Ar group in the compound of formula (1) to the rest of the molecule.

The compounds of the invention contain at least one asymmetric carbon atom and may exist as enantiomers (or as pairs of diastereoisomers) or as mixtures of such. Further, when n is 1, the compounds of the invention are sulphoxides, which can exists in two enantiomeric forms, and the adjacent carbon can also exists in two enantiomeric forms. Compounds of general formula (1) can therefore exist as racemates, diastereoisomers, or single enantiomers, and the invention includes all possible isomers or isomer mixtures in all proportions. It is to be expected that for any given compound, one isomer may be more fungicidally active than another.

Except where otherwise stated, alkyl groups and alkyl moieties of alkoxy, alkylthio, etc., suitably contain from 1 to 6, typically from 1 to 4, carbon atoms in the form of straight or branched chains. Examples are methyl, ethyl, n- and isopropyl and n-, sec-, iso- and tert-butyl. Where alkyl moieties contain 5 or 6 carbon atoms, examples are n-pentyl and n-hexyl. Examples of suitable optional substituents of alkyl groups and moieties include halo, hydroxy, $C_{1-4}$ alkoxy and $C_{1-4}$ alkoxy($C_{1-4}$)alkoxy, optionally substituted aryl and optionally substituted heteroaryl. Where the optional substituent is halo, the haloalkyl group or moiety is typically trichloromethyl or trifluoromethyl.

Except where otherwise stated, alkenyl and alkynyl moieties also suitably contain from 2 to 6, typically from 2 to 4, carbon atoms in the form of straight or branched chains. Examples are allyl, ethynyl and propargyl. Optional substituents include halo.

Halo includes fluoro, chloro, bromo and iodo. Most commonly it is fluoro, chloro or bromo and usually fluoro or chloro.

Aryl is usually phenyl but also includes naphthyl, anthryl and phenanthryl.

Heteroaryl is typically a 5- or 6-membered aromatic ring containing one or more O, N or S heteroatoms, which may be fused to one or more other aromatic or hetero-aromatic rings, such as a benzene ring. Examples are thienyl, furyl, pyrrolyl, isoxazolyl, oxazolyl, thiazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuranyl, benzothienyl, dibenzofuranyl, dibenzothienyl, benzothiazolyl, benzoxazolyl, benzimidazolyl, indolyl, quinolyl, isoquinolyl, quinazolinyl and quinoxalinyl groups and, where appropriate, N-oxides and salts thereof. Any of the aryl or heteroaryl values are optionally substituted. Except where otherwise stated, substituents which may be present include one or more of the following: halo, hydroxy, mercapto, $C_{1-6}$ alkyl (especially methyl and ethyl), $C_{2-6}$ alkenyl (especially allyl), $C_{2-6}$ alkynyl (especially propargyl), $C_{1-6}$ alkoxy (especially methoxy), $C_{2-6}$ alkenyloxy (especially allyloxy), $C_{2-6}$ alkynyloxy (especially propargyloxy), halo($C_{1-6}$)alkyl (especially trifluoromethyl), halo($C_{1-6}$)alkoxy (especially trifluoromethoxy), —$S(O)_m(C_{1-6})$alkyl wherein m is 0, 1 or 2 and the alkyl is optionally substituted with halo, hydroxy($C_{1-6}$)alkyl, $C_{1-4}$alkoxy($C_{1-4}$)alkyl, $C_{1-4}$alkoxy($C_{1-4}$)alkoxy, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted —$S(O)_m$aryl wherein m is 0, 1 or 2 (especially optionally substituted phenylthio), optionally substituted —$S(O)_m$heteroaryl wherein m is 0, 1 or 2 (especially optionally substituted pyridylthio or pyrimidinylthio), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridyl($C_{1-4}$)alkyl or pyrimidinyl($C_{1-4}$)alkyl), optionally substituted aryl($C_{2-4}$)alkenyl (especially optionally substituted phenylethenyl), optionally substituted heteroaryl($C_{2-4}$)-alkenyl (especially optionally substituted pyridylethenyl or pyrimidinylethenyl), optionally substituted aryl($C_{1-4}$)alkoxy (especially optionally substituted benzyloxy and phenethyloxy), optionally substituted heteroaryl($C_{1-4}$)alkoxy (especially optionally substituted pyridyl($C_{1-4}$)alkoxy or pyrimidinyl($C_{1-4}$)alkoxy), optionally substituted aryloxy($C_{1-4}$)alkyl (especially phenoxymethyl), optionally substituted heteroaryloxy-($C_{1-4}$)alkyl (especially optionally substituted pyridyloxy($C_{1-4}$)alkyl or pyrimidinyloxy-($C_{1-4}$)alkyl), optionally substituted —$S(O)_m(C_{1-4})$alkylaryl wherein m is 0, 1 or 2 (especially optionally substituted benzylthio and phenethylthio), optionally substituted —$S(O)_m(C_{1-4})$alkylheteroaryl wherein m is 0, 1 or 2 (especially optionally substituted pyridyl($C_{1-4}$)alkylthio or pyrimidinyl($C_{1-4}$)alkylthio), optionally substituted —($C_{1-4}$)alkylS$(O)_m$aryl wherein m is 0, 1 or 2 (especially phenylthiomethyl), optionally substituted —($C_{1-4}$)alkylS$(O)_m$heteroaryl wherein m is 0, 1 or 2 (especially optionally substituted pyridylthio($C_{1-4}$)alkyl or pyrimidinylthio($C_{1-4}$)alkyl), acyloxy, including $C_{1-4}$ alkanoyloxy (especially acetyloxy) and benzoyloxy, cyano, isocyano, thiocyanato, isothiocyanato, nitro, $NR^gR^h$, —$NHCOR^g$, —$NHCONR^gR^h$, —$CONR^gR^h$, —$CO_2R^g$, —$SO_2R^i$, —$OSO_2R^i$, —$COR^g$, —$CR^g$=$NR^h$ or —N=$CR^gR^h$ in which $R^i$ is $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy and $R^g$ and $R^h$ are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cyclo-alkyl($C_{1-4}$)alkyl, phenyl or benzyl, the phenyl and benzyl groups being optionally substituted with halogen, $C_{1-4}$ alkyl or $C_{1-4}$ alkoxy.

Of particular interest are compounds (1) where Ar is a group of the formula (A) and $A^1$ is aryloxy or heteroaryloxy, especially phenoxy and pyridyloxy. Of more particular interest are compounds (1) where Ar is a group of the formula (A) and $A^1$ is aryloxy, especially phenoxy. Of especial interest are compounds (1) where Ar is 3-phenoxyphenyl and 4-phenoxyphenyl, in particular compounds (1) where Ar is 3-phenoxyphenyl.

Of particular interest are compounds (1) where Ar is a group of the formula (A) and $A^1$ and $A^2$ together form a 5-membered unsaturated ring where one carbon atom is replaced with an O atom and the unsaturated 5 membered ring is fused with a benzene ring to form dibenzofuran-2-yl which can be optionally substituted with halo or $C_{1-4}$ alkyl.

Of more particular interest are compounds (1) where Ar is a group of the formula (A) and $A^1$ and $A^2$ together form a 5-membered unsaturated ring where one carbon atom is replaced with an O atom and the unsaturated 5 membered ring is fused with a benzene ring to form dibenzofuran-2-yl which can be optionally substituted with halo, in particular chloro or bromo, or $C_{1-4}$ alkyl, in particular methyl.

Another group of interesting compounds are those wherein Ar is benzofuranyl or benzothiophenyl.

Of particular interest are compounds (1) where Ar is a group of the formula (B1) or (B2) are the compounds where, M is N and L is CQ (quinolinyl). Also of interest are those compounds (1) where L is N and M is CQ (isoquinolinyl) and those compounds (1) where L and M are both CQ (naphthyl). V is typically H, halo or methyl; most typically H. $K^a$ and $K^b$ are typically H. And Q is typically aryl, for example phenyl, or aryl($C_{1-4}$)-alkoxy, for example benzyloxy. Preferred are compounds (1) where the quinolinyl is attached via the 6 position, for example 3-phenylquinolin-6-yl.

$R^1$ is typically methyl.

$R^2$ is typically H.

$R^2$ also includes $C_{1-4}$ alkoxy($C_{1-4}$)alkyl, especially $C_{1-4}$ alkoxymethyl, and aryl-oxy($C_{1-4}$)alkyl, especially benzyloxymethyl, in which the phenyl ring of the benzyl group optionally carries one, two or three alkoxy substituents, e.g. a methoxy substituent.

$R^3$ and $R^4$ are typically both methyl. However, they can have different values, for example $R^3$ can be ethyl and $R^4$ can be methyl.

Typically $R^5$ is H, methyl or methoxymethyl, preferably H or methyl Another group of interesting compounds are those wherein Ar is benzofuran-5-yl, benzothiophen-5-yl, benzofuran-6-yl or benzothiophen-6-yl, $R^1$, $R^3$ and $R^4$ are methyl, $R^2$ is H, $R^5$ is H or methyl and n is 0.

Compounds that form part of the invention are illustrated in Tables 1 to 72 below.

TABLE 1

The compounds in Table 1 are of the general formula (1) where Ar is 3-phenoxyphenyl, n is 0, $R^1$ is methyl, $R^2$ is H, and $R^3$, $R^4$ and $R^5$ have the values given in the table.

| Compound. No. | $R^3$ | $R^4$ | $R^5$ |
|---|---|---|---|
| 1 | CH₃— | CH₃— | H |
| 2 | CH₃— | C₂H₅— | H |
| 3 | —CH₂CH₂— | | H |
| 4 | CH₃— | CH₃— | CH₃— |
| 5 | CH₃— | C₂H₅— | CH₃— |
| 6 | —CH₂CH₂— | | CH₃— |
| 7 | CH₃ | CH₃ | CH₃OCH₂— |
| 8 | CH₃ | CH₃ | CH₃OC₂H₄— |
| 9 | CH₃ | CH₃ | C₂H₅OC₂H₄— |
| 10 | CH₃ | CH₃ | CH₃OC₂H₄OC₂H₄— |
| 11 | CH₃ | CH₃ | Cl-n-C₃H₆— |
| 12 | CH₃ | CH₃ | NC-n-C₃H₆— |
| 13 | CH₃ | CH₃ | CH₃SCH₂— |
| 14 | CH₃ | CH₃ | C₆H₅— |
| 15 | CH₃ | CH₃ | (CH₃)₂(CH₃O)C— |

¹H NMR characterisation of compound number 4 of Table 1 (2-(3-phenoxyphenoxy)-2-methylthio-N-(2-methylpent-3-yn-2-yl) acetamide) is provided on page 39.

TABLE 2

The compounds in Table 2 are of the general formula (1) where Ar is indan-5-yl, n is 0, $R^1$ is methyl, $R^2$ is H, and $R^3$, $R^4$ and $R^5$ have the values given in Table 1. Thus there are 15 compounds in Table 2, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH₃— | CH₃— | CH₃— | Oil |

The preparation of compound No. 4 (2-(indanyl-5-oxy)-2-methylthio-N -(2-methylpent-3-yn-2-yl) acetamide) of Table 2 is described in Example 2, pages 38-39. ¹H NMR data for compound No. 4 of Table 2 are provided on page 39.

Table 3

The compounds in Table 3 are of the general formula (1) where Ar is 1,3-benzodioxol-5-yl, n is 0, $R^1$ is methyl, $R^2$ is H, and $R^3$, $R^4$ and $R^5$ have the values given in Table 1. Thus there are 15 compounds in Table 3, compound 1 having the same values of $R^3$, $R^4$ and $R^5$ as compound 1 in Table 1, compound 2 having the same values of $R^3$, $R^4$ and $R^5$ as compound 2 in Table 1, and so on.

¹H NMR characterisation of compound number 4 of Table 3 (2-(3,4-methylenedioxy-phenoxy)-2-methylthio-N-(2-methylpent-3-yn-2-yl)acetamide) is provided on page 39.

Table 4

The compounds in Table 4 are of the general formula (1) where Ar is 2-oxo-1,3-benzodioxol-5-yl, n is 0, $R^1$ is methyl, $R^2$ is H, and $R^3$, $R^4$ and $R^5$ have the values given in Table 1. Thus there are 15 compounds in Table 4, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 5

The compounds in Table 5 are of the general formula (1) where Ar is 2-thioxo-1,3-benzodioxol-5-yl, n is 0, $R^1$ is methyl, $R^2$ is H, and $R^3$, $R^4$ and $R^5$ have the values given in Table 1. Thus there are 15 compounds in Table 5, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 6

The compounds in Table 6 are of the general formula (1) where Ar is 1,3-benzoxathiol-5-yl, n is 0, $R^1$ is methyl, $R^2$ is H, and $R^3$, $R^4$ and $R^5$ have the values given in Table 1. Thus there are 15 compounds in Table 6, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 7

The compounds in Table 7 are of the general formula (1) where Ar is 2-oxo-1,3-benzoxathiol-5-yl, n is 0, $R^1$ is methyl, $R^2$ is H, and $R^3$, $R^4$ and $R^5$ have the values given in Table 1. Thus there are 90 compounds in Table 7, compound 1 having the same values of $R^3$, $R^4$ and $R^5$ as compound 1 in Table 1, compound 2 having the same values of $R^3$, $R^4$ and $R^5$ as compound 2 in Table 1, and so on.

¹H NMR characterisation of compound number 4 of Table 7 (5-(2-oxo-1,3-benzoxathiolyl)-2-methylthio-N-(2-methylpent-3-yn-2-yl)acetamide) is provided on page 39/40.

Table 8

The compounds in Table 8 are of the general formula (1) where Ar is 1,3-benzodithiol-5-yl, n is 0, $R^1$ is methyl, $R^2$ is H, and $R^3$, $R^4$ and $R^5$ have the values given in Table 1. Thus there are 15 compounds in Table 8, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 9

The compounds in Table 9 are of the general formula (1) where Ar is inden-5-yl, n is 0, $R^1$ is methyl, $R^2$ is H, and $R^3$, $R^4$ and $R^5$ have the values given in Table 1. Thus there are 15 compounds in Table 9, compound 1 having the same values of $R^3$, $R^4$ and $R^5$ as compound 1 in Table 1, compound 2 having the same values of $R^3$, $R^4$ and $R^5$ as compound 2 in Table 1, and so on.

TABLE 10

The compounds in Table 10 are of the general formula (1) where Ar is benzofuran-5-yl, n is 0, $R^1$ is methyl, $R^2$ is H, and $R^3$, $R^4$ and $R^5$ have the values given in Table 1. Thus there are 15 compounds in Table 10, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 1 | CH$_3$— | CH$_3$— | H | oil |
| 4 | CH$_3$— | CH$_3$— | CH$_3$— | oil |

Table 11

The compounds in Table 11 are of the general formula (1) where Ar is 2-phenyl-benzofuran-5-yl, n is 0, $R^1$ is methyl, $R^2$ is H, and $R^3$, $R^4$ and $R^5$ have the values given in Table 1. Thus there are 15 compounds in Table 11, compound 1 having the same values of $R^3$, $R^4$ and $R^5$ as compound 1 in Table 1, compound 2 having the same values of $R^3$, $R^4$ and $R^5$ as compound 2 in Table 1, and so on.

TABLE 12

The compounds in Table 12 are of the general formula (1) where Ar is 3-methyl-benzofuran-5-yl, n is 0, $R^1$ is methyl, $R^2$ is H, and $R^3$, $R^4$ and $R^5$ have the values given in Table 1. Thus there are 15 compounds in Table 12, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH$_3$— | CH$_3$— | CH$_3$— | oil |

TABLE 13

The compounds in Table 13 are of the general formula (1) where Ar is benzothiophen-5-yl, n is 0, $R^1$ is methyl, $R^2$ is H, and $R^3$, $R^4$ and $R^5$ have the values given in Table 1. Thus there are 15 compounds in Table 13, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH$_3$— | CH$_3$— | CH$_3$— | oil |

Table 14

The compounds in Table 14 are of the general formula (1) where Ar is 9H-fluoren-3-yl, n is 0, $R^1$ is methyl, $R^2$ is H, and $R^3$, $R^4$ and $R^5$ have the values given in Table 1. Thus there are 15 compounds in Table 14, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 15

The compounds in Table 15 are of the general formula (1) where Ar is 9-oxo-9H-fluoren-3-yl, n is 0, $R^1$ is methyl, $R^2$ is H, and $R^3$, $R^4$ and $R^5$ have the values given in Table 1. Thus there are 15 compounds in Table 15, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 16

The compounds in Table 16 are of the general formula (1) where Ar is dibenzofuran-2-yl, n is 0, $R^1$ is methyl, $R^2$ is H, and $R^3$, $R^4$ and $R^5$ have the values given in Table 1. Thus there are 15 compounds in Table 16, compound 1 having the same values of $R^3$, $R^4$ and $R^5$ as compound 1 in Table 1, compound 2 having the same values of $R^3$, $R^4$ and $R^5$ as compound 2 in Table 1, and so on.

The preparation of compound No. 4 of Table 16 (2-(dibenzofuranyl-2-oxy)-2-methylthio-N-(2-methylpent-3-yn-2-yl)acetamide) is described in Example 1, page 35-37. Melting point and 1H NMR data for compound No. 4 of Table 16 are provided on page 37. 1H NMR characterisation of compound numbers 1, 5 and 7 of Table 16 is provided on page 38.

Table 17

The compounds in Table 17 are of the general formula (1) where Ar is 7-methyl-dibenzofuran-2-yl, n is 0, $R^1$ is methyl, $R^2$ is H, and $R^3$, $R^4$ and $R^5$ have the values given in Table 1. Thus there are 15 compounds in Table 17, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 18

The compounds in Table 18 are of the general formula (1) where Ar is 8-chloro-dibenzofuran-2-yl, n is 0, $R^1$ is methyl, $R^2$ is H, and $R^3$, $R^4$ and $R^5$ have the values given in Table 1. Thus there are 15 compounds in Table 18, compound 1 having the same values of $R^3$, $R^4$ and $R^5$ as compound 1 in Table 1, compound 2 having the same values of $R^3$, $R^4$ and $R^5$ as compound 2 in Table 1, and so on.

The preparation of compound No. 4 of Table 18 (2-(8-chlorodibenzofuranyl-2-oxy)-2-methylthio-N-(2-methylpent-3-yn-2-yl)acetamide) is described in Example 1, page 37. $^1$H NMR data are provided on page 37.

TABLE 19

The compounds in Table 19 are of the general formula (1) where Ar is 9-chloro-dibenzofuran-2-yl, n is 0, $R^1$ is methyl, $R^2$ is H, and $R^3$, $R^4$ and $R^5$ have the values given in Table 1. Thus there are 15 compounds in Table 19, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH$_3$— | CH$_3$— | CH$_3$— | 119-120° C. |
| 7 | CH$_3$— | CH$_3$— | CH$_3$OCH$_2$— | oil |
| 8 | CH$_3$ | CH$_3$ | CH$_3$OC$_2$H$_4$— | 105° C. |

Table 20

The compounds in Table 20 are of the general formula (1) where Ar is dibenzothiophen-2-yl, n is 0, $R^1$ is methyl, $R^2$ is H, and $R^3$, $R^4$ and $R^5$ have the values given in Table 1.

Thus there are 15 compounds in Table 20, compound 1 having the same values of $R^3$, $R^4$ and $R^5$ as compound 1 in Table 1, compound 2 having the same values of $R^3$, $R^4$ and $R^5$ as compound 2 in Table 1, and so on.

The preparation of compound No. 4 of Table 20 (2-(dibenzothienyl-2-oxy)-2-methylthio-N-(2-methylpent-3-yn-2-yl)acetamide) is described in Example 1, page 37. $^1$H NMR data is provided on page 38.

TABLE 21

The compounds in Table 21 are of the general formula (1) where Ar is 5,6,7,8-tetrahydronaphth-2-yl, n is 0, $R^1$ is methyl, $R^2$ is H, and $R^3$, $R^4$ and $R^5$ have the values given in Table 1. Thus there are 15 compounds in Table 21, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 1 | CH$_3$— | CH$_3$— | H | oil |
| 4 | CH$_3$— | CH$_3$— | CH$_3$— | oil |

Table 22

The compounds in Table 22 are of the general formula (1) where Ar is 3-phenyl-quinolin-6-yl of the formula (B1), n is 0, $R^1$ is methyl, $R^2$ is H, and $R^3$, $R^4$ and $R^5$ have the values given in Table 1. Thus there are 15 compounds in Table 22, compound 1 having the same values of $R^3$, $R^4$ and $R^5$ as compound 1 in Table 1, compound 2 having the same values of $R^3$, $R^4$ and $R^5$ as compound 2 in Table 1, and so on.

The preparation of compound No. 4 of Table 22 (2-(3-phenylquinolinyl -6-oxy)-2-methylthio-N-(2-methylpent-3-yn-2-yl)acetamide) is described in Example 3, pages 40-41. $^1$H NMR data is provided on page 41.

Table 23

The compounds in Table 23 are of the general formula (1) where Ar is 3-benzyl-quinolin-6-yl of the formula (B1), n is 0, $R^1$ is methyl, $R^2$ is H, and $R^3$, $R^4$ and $R^5$ have the values given in Table 1. Thus there are 15 compounds in Table 23, compound 1 having the same values of $R^3$, $R^4$ and $R^5$ as compound 1 in Table 1, compound 2 having the same values of $R^3$, $R^4$ and $R^5$ as compound 2 in Table 1, and so on.

Table 24

The compounds in Table 24 are of the general formula (1) where Ar is 7-benzyloxy-naphth-2-yl of the formula (B1), n is 0, $R^1$ is methyl, $R^2$ is H, and $R^3$, $R^4$ and $R^5$ have the values given in Table 1. Thus there are 15 compounds in Table 24, compound 1 having the same values of $R^3$, $R^4$ and $R^5$ as compound 1 in Table 1, compound 2 having the same values of $R^3$, $R^4$ and $R^5$ as compound 2 in Table 1, and so on.

The preparation of compound No. 4 of Table 24 (2-(2-benzyloxynaphthyl -7-oxy)-2-methylthio-N-(2-methylpent-3-yn-2-yl)acetamide) is described in Example 4, page 41. $^1$H NMR data is provided on page 42.

TABLE 24A

The compounds in Table 73 are of the general formula (1) where Ar is benzofuran-6-yl, n is 0, $R^1$ is methyl, $R^2$ is H, and $R^3$, $R^4$ and $R^5$ have the values given in Table 1. Thus there are 15 compounds in Table 73, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH$_3$— | CH$_3$— | CH$_3$— | oil |

TABLE 24B

The compounds in Table 74 are of the general formula (1) where Ar is benzothiophen-6-yl, n is 0, $R^1$ is methyl, $R^2$ is H, and $R^3$, $R^4$ and $R^5$ have the values given in Table 1. Thus there are 15 compounds in Table 73, compound 1 having the same values of $R^3$, $R^4$ and $R^5$ as compound 1 in Table 1, compound 2 having the same values of $R^3$, $R^4$ and $R^5$ as compound 2 in Table 1, and so on.

| Compound No. | $R^3$ | $R^4$ | $R^5$ | |
|---|---|---|---|---|
| 4 | CH$_3$— | CH$_3$— | CH$_3$— | oil |

Tables 25 to 50

Tables 25 to 50 correspond exactly to Tables 1 to 24B (i.e. Table 25 corresponds exactly to Table 1, Table 26 corresponds exactly to Table 2, and so on) the only difference being that in each of Tables 25 to 50 n is 1 instead of 0.

TABLE 34

Table 34 corresponds exactly to Table 10 the only difference being that in Table 34, n is 1 instead of 0.

| Compound No. | $R^3$ | $R^4$ | $R^5$ | |
|---|---|---|---|---|
| 1 | CH$_3$— | CH$_3$— | H | oil |
| 4 | CH$_3$— | CH$_3$— | CH$_3$— | oil |

Tables 51 to 76

Tables 49 to 72 correspond exactly to Tables 1 to 24 (i.e. Table 49 corresponds exactly to Table 1, Table 50 corresponds exactly to Table 2, and so on) the only difference being that in each of Tables 49 to 72 n is 2 instead of 0.

TABLE 60

Table 60 corresponds exactly to Table 10 the only difference being that in Table 60, n is 2 instead of 0.

| Compound No. | $R^3$ | $R^4$ | $R^5$ | |
|---|---|---|---|---|
| 1 | CH$_3$— | CH$_3$— | H | oil |
| 4 | CH$_3$— | CH$_3$— | CH$_3$— | oil |

The compounds of general formula (1) may be prepared as outlined in Schemes 1 to 5 below, in which Ar, $R^1$, $R^2$, $R^3$, $R^4$, $R^5$ and n have the meanings given above, $R^6$ is H or $C_{1-4}$ alkyl, as indicated, $R^a$ is H or $C_{1-3}$ alkyl, $R^b$ is H or $C_{1-3}$ alkyl provided that when $R^a$ and $R^b$ are both alkyl their total number of carbon atoms does not exceed 3, $R^c$ is $C_{1-6}$ alkyl, $C_{1-3}$ alkoxy($C_{1-3}$)alkyl, optionally substituted aryl, optionally substituted aryl($C_{1-4}$)-alkyl, optionally substituted heteroaryl or optionally substituted heteroaryl($C_{1-4}$)alkyl, DMF is N,N-dimethylformamide, NBS is N-bromosuccinimide, NCS is N-chlorosuccinimide and MCPBA is m-chloroperbenzoic acid. Other abbreviations are defined in the text.

Compounds of formula (1), where n is 0, may be prepared as shown in Scheme 1. Esters of formula (2), where $R^6$ is $C_{1-4}$ alkyl, may be halogenated to give haloesters of formula (3), where Hal is a halogen atom such as bromine, chlorine or iodine, by reaction with a halogenating agent such as N-bromosuccinimide or N-chlorosuccinimide, in a suitable solvent such as carbon tetrachloride or acetonitrile, in the presence of a radical initiator such as AIBN (azo-isobutyronitrile), and a light source, at between ambient temperature and the reflux temperature of the solvent. Compounds of general formula (3) are then reacted with alkanethiols of general formula $R^1$SH, in the presence of a base such as sodium hydride, in a suitable solvent such as DMF, to give compounds of general formula (6), or are reacted with alkanethiol salts $R^1S^-M^+$, where M is a metal such as sodium or lithium, in a suitable solvent such as DMF, to give compounds of general formula (6).

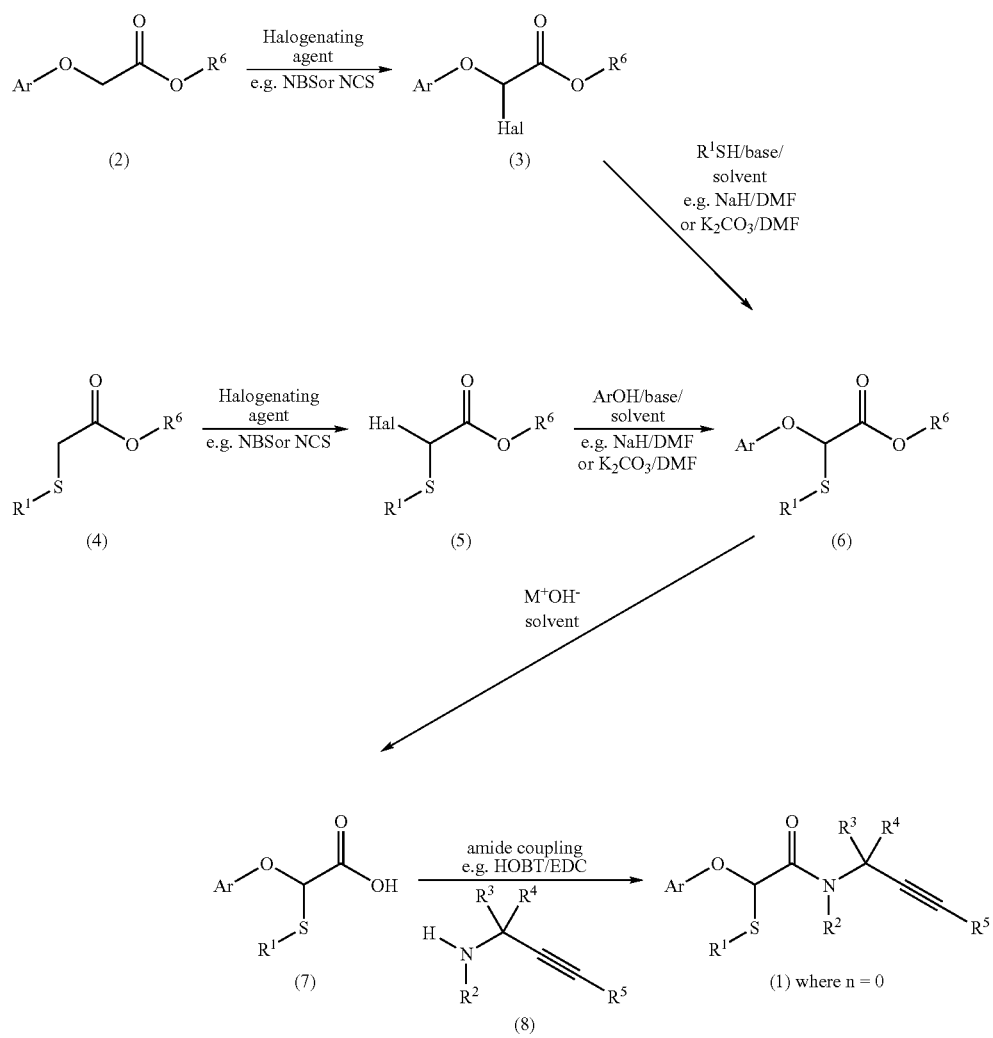

Scheme 1

Alternatively esters of general formula (4) are halogenated to give haloesters of formula (5), where Hal is a halogen atom such as bromine, chlorine or iodine, by reaction with a halogenating agent such as N-chlorosuccinimide, N-bromosuccinimide or sulfuryl chloride, in a suitable solvent such as carbon tetrachloride or acetonitrile, at between 0° C. and the reflux temperature of the solvent. Haloesters of formula (5) are reacted with hydroxy(hetero)aryls ArOH, where Ar is as defined above, in the presence of a base such as potassium t-butoxide, potassium carbonate, or sodium hydride in a suitable solvent such as t-butanol, 1,4-dioxane or DMF, at between ambient temperature and the reflux temperature of the solvent, to give compounds of formula (6). Compounds of formula (6) are hydrolysed to acids of formula (7) by reaction with an alkali metal hydroxide M⁺OH⁻, in a suitable solvent such as aqueous methanol, ethanol, or THF (tetrahydrofuran) at between ambient temperature and the reflux temperature of the solvent. Acids of formula (7) can be condensed with amines of formula (8), using suitable activating agents such as HOBT (1-hydroxybenzotriazole) and EDC (1-ethyl-3-N,N-dimethylaminopropyl -carbodiimide hydrochloride), at between 0° C. and ambient temperature, to give compounds of general formula (1) where n is 0.

Compounds of general formula (1), where n is 1 or 2, are prepared by oxidation to the sulphoxide (n is 1) or sulphone (n is 2) oxidation state, as shown in Scheme 2. For example, esters of the general formula (6) can be oxidised to sulphoxides of formula (9) with an oxidising agent such as sodium periodate in a suitable solvent such ethanol, between 0° C. and ambient temperature. Sulphones of formula (10) can be made either directly from compounds of formula (6) with two or more equivalents of an oxidising agent such as m-chloroperbenzoic acid (MCPBA), in a suitable solvent such as dichloro-methane between 0° C. and the reflux temperature of the solvent, or from sulphoxides of formula (9) with one or more equivalents of m-chloroperbenzoic acid. Sulphides of formula (6), sulphoxides of formula (9) or sulphones of formula (10) can be hydrolysed to the corresponding acids (7), (11) or (12) by reaction with an alkali metal hydroxide in a suitable solvent such as ethanol at between 0° C. and the reflux temperature of the solvent followed by acidification. The acids of formula (7), (11) or (12) can be condensed with amines of formula (8), using suitable activating agents such as HOBT and EDC, at between 0° C. and ambient temperature, to give compounds of general formula (1) where n is 0, 1 or 2.

Scheme 2

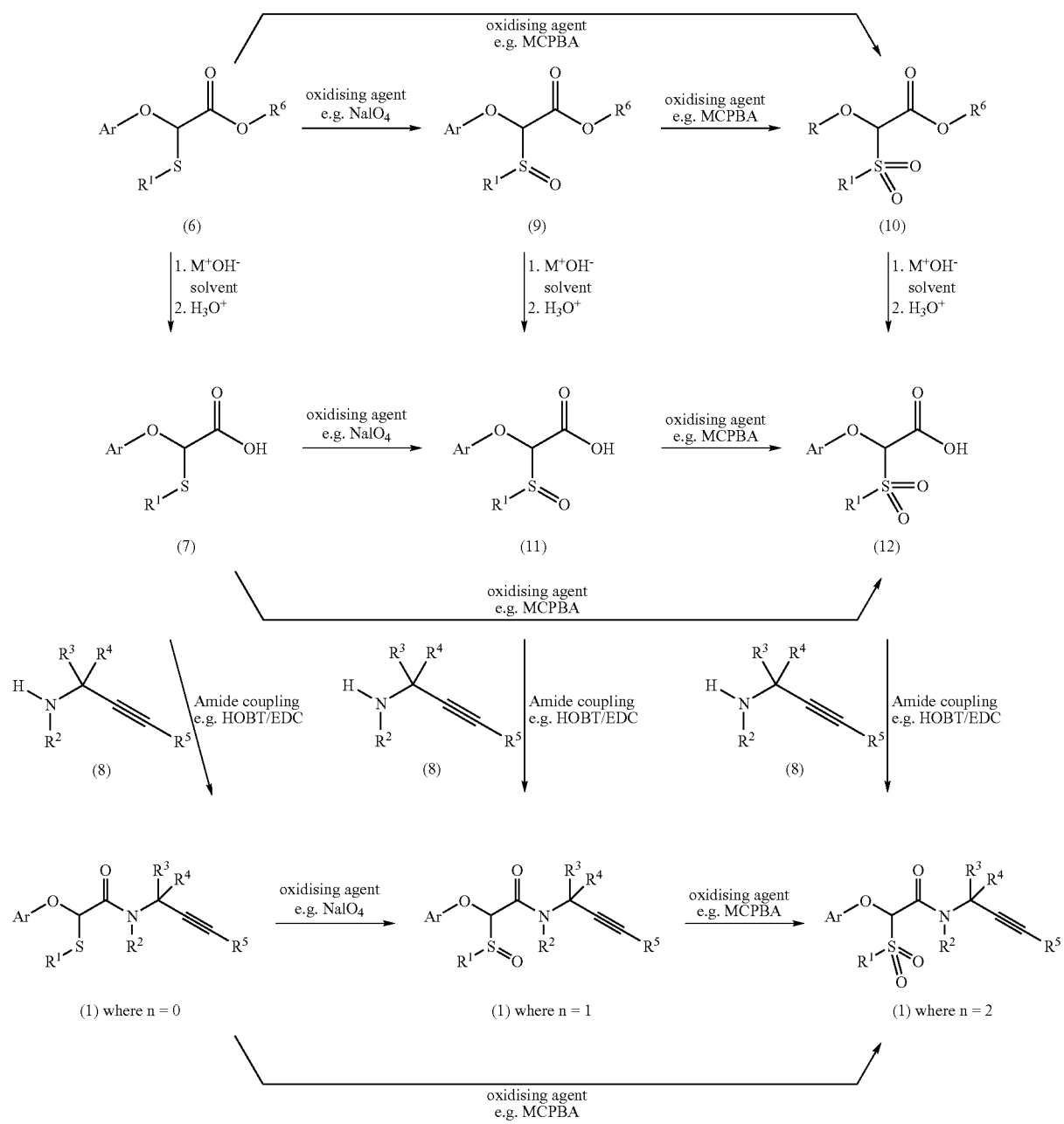

Similarly, sulphoxides of formula (11) and of formula (1) where n is 1 can be prepared from sulphides of formula (7) and of formula (1) where n is 0 respectively, using oxidising agents such as sodium metaperiodate or m-chloroperbenzoic acid as described above. Sulphones of formula (12) and of formula (1) where n is 2, can be prepared either from sulphides of formula (7) and of formula (1) where n is 0, by using at least two equivalents of oxidising agents such as m-chloroperbenzoic acid, or from sulphoxides of formula (11) and of formula (1) where n is 1, using one or more equivalents of oxidising agents such as m-chloroperbenzoic acid, as described above.

Compounds of formula (1) can also be prepared as shown in Scheme 3 where n=0. Acids of formula (13) can be condensed with amines of formula (8), using suitable activating agents such as HOBT and EDC, at between 0° C. and ambient temperature, to give compounds of formula (14). Compounds of formula (14) can be halogenated to compounds of formula (16) using a halogenating agent such as N-bromosuccinimide or N-chlorosuccinimide, in a suitable solvent such as carbon tetrachloride or acetonitrile, at between 0° C. and ambient temperature. Amides of formula (16) can also be prepared from acid halides of formula (15) by reaction with amines of formula (8) in the presence of a base such as triethylamine in a suitable solvent such as dichloromethane, at between 0° C. and ambient temperature.

Scheme 3

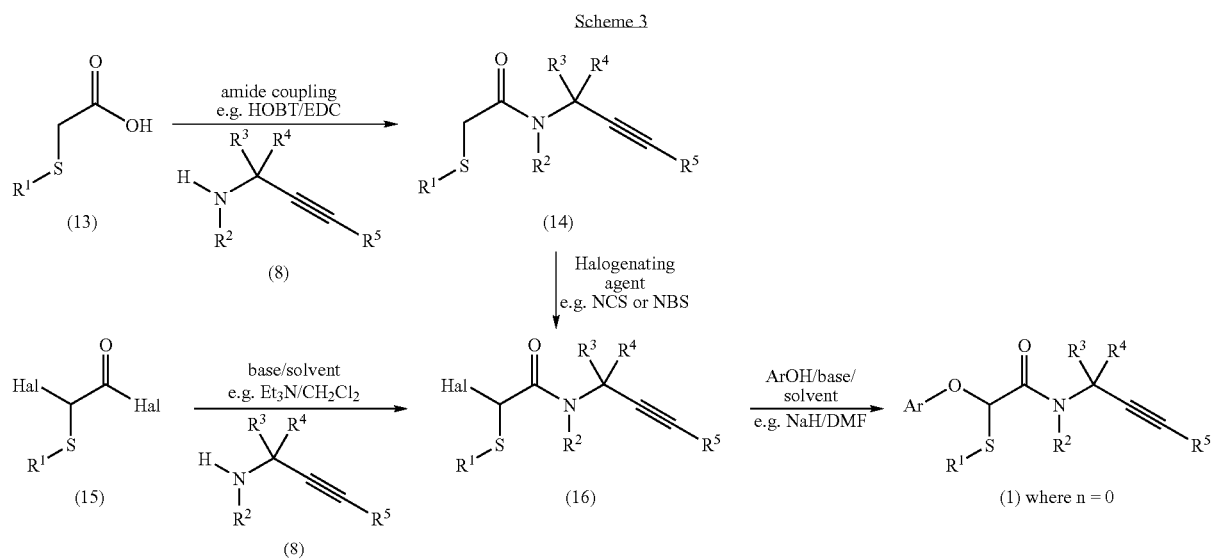

Halosulphides of formula (16) can be reacted with hydroxy (hetero)aryls ArOH, in the presence of a base such as potassium carbonate or sodium hydride, in a suitable solvent such as DMF, at between 0° C. and 80° C., to give compounds of formula (1) where n is 0.

Hydroxy(hetero)aryls ArOH are either commercially available or may be prepared by standard literature methods (see, for example, Synthesis, 1999, 7, 1181-1187 for the preparation of benzofuran-5-ol used for the preparation of compounds in Table 10; Synthetic Communications 1991, 21(7), 959-64 for the preparation of benzo[b]thiophen-5-ol used for the preparation of compounds in Table 13; Journal of Medicinal Chemistry 2004, 47(20), 4829-4837 for the preparation of benzofuran-6-ol used for the preparation of compounds in Table 24A; Journal of the Chemical Society, Perkin Transactions 1: Organic and Bio-Organic Chemistry (1972- 1999) (1982), (3), 815-21 for the preparation of benzo[b]thiophen-6-ol used for the preparation of compounds in Table 24B).

As shown in Scheme 4, silyl-protected aminoalkynes of the general formula (18) may be obtained by reacting amines of general formula (17) with 1,2-bis-(chloro -dimethylsilyl) ethane in the presence of a suitable base, such as a tertiary organic amine base, for example, triethylamine. Amines of the general formula (20), which are examples of amines of the general formula (8) wherein $R^2$ is H, may be prepared by alkylation of a silyl-protected aminoalkyne of the general formula (18) using a suitable base, such as n-butyl lithium, followed by reaction with a suitable alkylating reagent $R^5LG$, such as an alkyl iodide, for example, methyl iodide, to form an alkylated compound of the general formula (19). The silyl protecting group may then be removed from a compound of the general formula (19) with, for example, an aqueous acid to form an aminoalkyne of the general formula (20).

Scheme 4

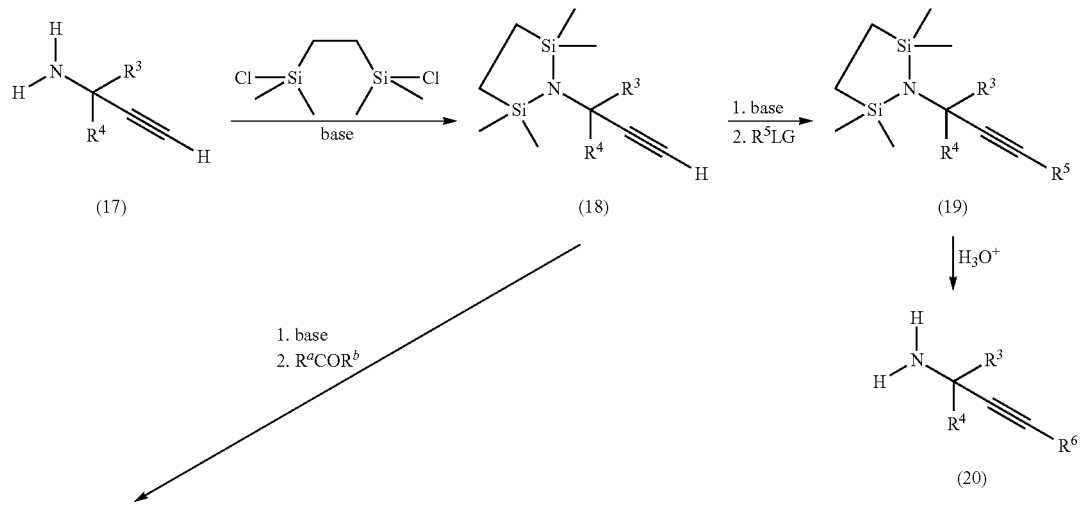

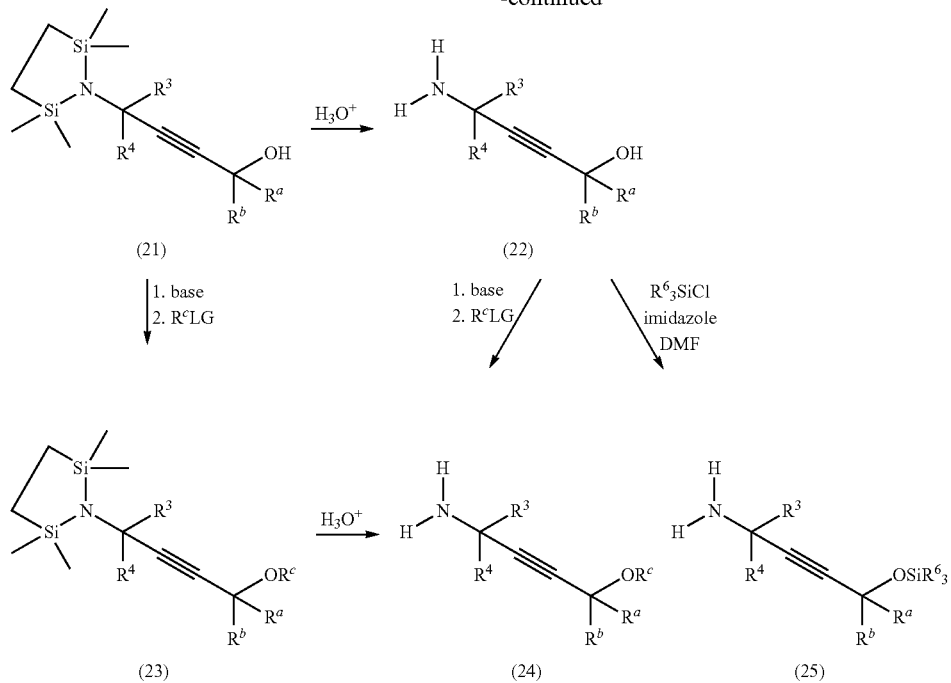

In a similar procedure, a silyl-protected aminoalkyne of the general formula (18) may be reacted with a carbonyl derivative $R^aCOR^b$, for example formaldehyde, using a suitable base, such as n-butyl lithium, to provide an aminoalkyne (21) containing a hydroxyalkyl moiety. A compound of the general formula (21) may either first be treated with a base, such as sodium hydride or potassium bis(trimethylsilyl)amide followed by a compound $R^cLG$, where LG represents a leaving group such as a halogen, or sulphonate ester such as $OSO_2Me$, or $OSO_2$-4-tolyl, for example ethyl iodide, to give a compound of the general formula (23). After removal of the silyl protecting group, compounds of general formula (24) are obtained. Alternatively, the silyl protecting group can first be removed to yield compounds of the general formula (22). Aminoalkynes of the general formula (22) may be further derivatised by reacting with a silylating agent, for example t-butyldimethylsilyl chloride, to give a derivative silylated on oxygen of the general formula (25).

Scheme 5

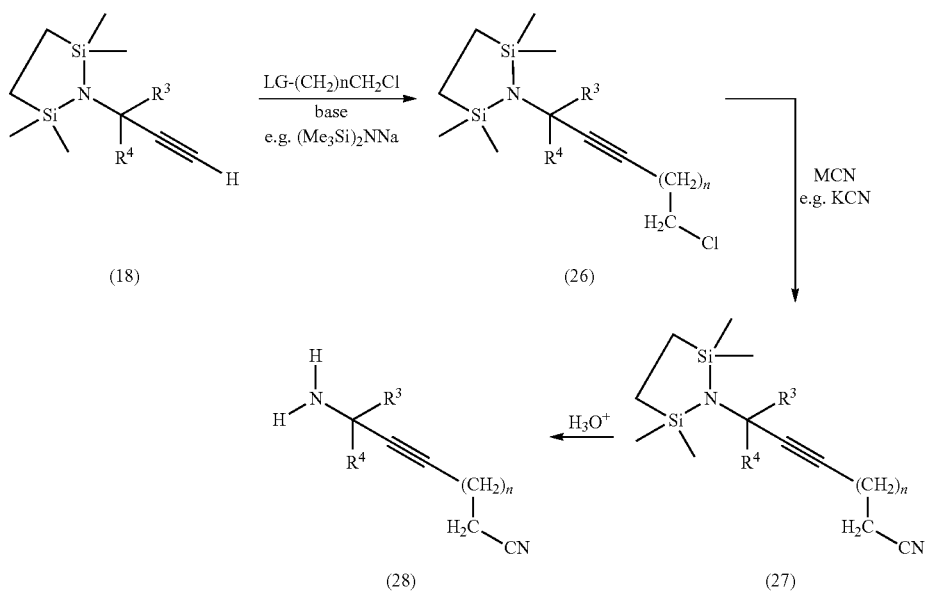

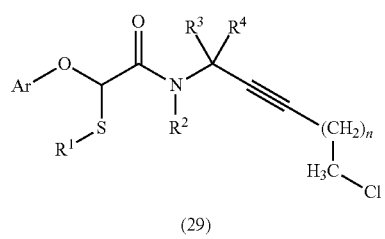 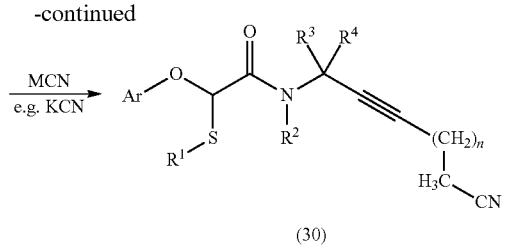

As shown in Scheme 5, silyl-protected aminoalkynes of the general formula (26) may be obtained by reacting silyl-protected amines of general formula (18) with chloro-alkanes bearing a suitable leaving group, for example bromide or iodide, in the presence of a suitable base, such as a sodium or lithium amide base, for example, sodium bis(trimethylsilyl)amide or sodium amide. Amines of the general formula (28), which are examples of amines of the general formula (8) wherein $R^2$ is H, may be prepared by displacement of chloride anion by cyanide, followed by removal of the silyl protecting group with, for example, an aqueous acid, to form a cyano compound of the general formula (28).

In a similar procedure, an amide of the general formula (29) can be reacted with, for example, potassium cyanide yielding a cyano amidoalkyne of the general formula (30).

As shown in Scheme 6, compounds of the general formula (1), wherein $R_5$ is H, may be reacted under Sonogashira conditions with, for example, optionally substituted aryl or heteroaryl chlorides, bromides, iodides or triflates to form substituted aryl or heteroaryl compounds of general formula (1), wherein $R_5$ is an optionally substituted aryl or heteroaryl group. A suitable palladium catalyst is tetrakis(triphenylphosphine)-palladium(0).

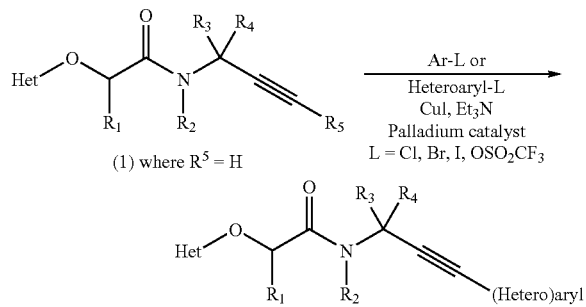

Amines of the general formula (17) are either commercially available or may be prepared by standard literature methods (see, for example, EP-A-0834498).

The compounds of formula (1) are active fungicides and may be used to control one or more of the following pathogens: *Pyriculayia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei*, *Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochiobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannonyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymnella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascocdyta* spp. on peas, wheat, barley and other hosts; *Stemphylium* spp. (*Pleospora* spp.) on apples, pears, onions and other hosts; sunmmer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juitiperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobdsidium theobromae* on cocoa causing vascular streak dieback; *Fusarium* spp., *Typhula* spp., *Microdochium nivale*, *Ustilago* spp., *Urocystis* spp., *Tilletia* spp. and *Claviceps*

*purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoniza piceae, Penicillium* spp., *Trichoderma pseudokonizngii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (1) show particularly good activity against the Oomycete class of pathogens such as *Phytophthora infestans, Plasmopara* species, e.g. *Plasmopara viticola* and *Pythium* species e.g. *Pythium ultimum.*

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.000 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmoriilonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (1) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed-space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuc-cinamates, paraffin or olefin sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition;

Examples of fungicidal compounds which may be included in the composition of the invention are AC 382042 (N-(1-cyano-1,2-dimethylpropyl)-2-(2,4-dichlorophenoxy) propionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupiriniate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquino-late, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxycarbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, trifnumizole, triforine, triticonazole, validamycin A, vapam, vinclozolin, XRD-563, zineb, ziram, zoxamide and compounds of the formulae:

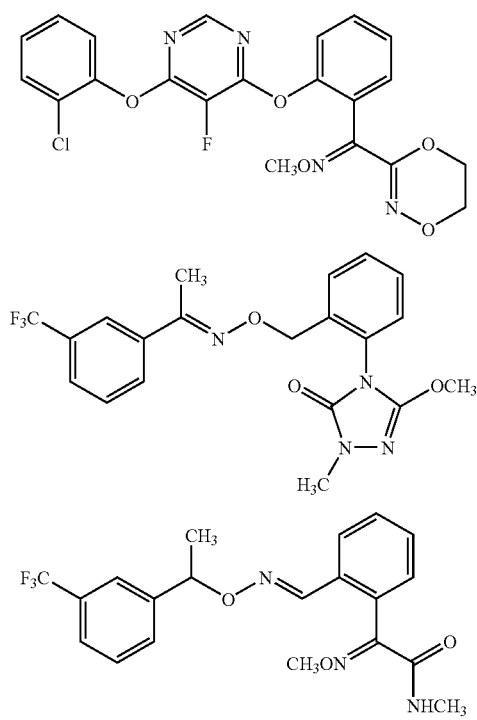

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:

| | | | |
|---|---|---|---|
| ml = | millilitres | m.p. = | melting point (uncorrected) |
| g = | grammes | b.p. = | boiling point |
| THF = | tetrahydrofuran | DMSO = | dimethylsulphoxide |
| M+ = | mass ion | DMF = | N, N-dimethylformamide |
| s = | singlet | HOBT = | 1-hydroxybenzotriazole |
| d = | doublet | EDC = | 1-ethyl-3-N,N-dimethylamino |
| bs = | broad singlet | | propylcarbodiimide hydrochloride |
| t = | triplet | HOAT = | 7-aza-1-hydroxybenzotriazole |
| q = | quartet | NMR = | nuclear magnetic resonance |
| m = | multiplet | HPLC = | high performance liquid chromatography |
| ppm = | parts per million | | |
| M = | molar | TLC = | thin layer chromatography |
| dec. = | decomposition | glc = | gas-liquid chromatography |

EXAMPLE 1

This Example illustrates the preparation of 2-(dibenzofuranyl-2-oxy)-2-methylthio-N-(2-methylpent-3-yn-2-yl)acetamide (Compound No. 4 of Table 16)

Stage 1: Preparation of ethyl 2-bromo-2-methylthioacetate

To a stirred solution of ethyl 2-methylthioacetate (40.2 g) in carbon tetrachloride (250 ml) at 15° C. was added in portions N-bromosuccinimide (NBS, 54 g) maintaining the reaction temperature below 20° C. during the addition. The mixture was stirred for 5 hours then further NBS (10 g) was added in portions and the reaction stirred for a further 18 hours. The mixture was washed with aqueous sodium carbonate then brine, dried over magnesium sulfate, filtered and the solvent evaporated under reduced pressure to give (56 g) as an orange liquid containing 10% of unreacted ethyl 2-methylthioacetate. The product was used in the next Stage without further purification. An analytical sample of ethyl 2-bromo-2-methylthioacetate was obtained by vacuum distillation, b.p. 54-56° C. at 0.1 mmHg.

$^1$H No (CDCl$_3$) δ ppm: 1.30 (3H, s); 2.34 (3H, s); 4.26 (2H, q); 5.39 (1H, s).

Stage 2: Preparation of ethyl 2-(dibenzofuranyl-2-oxy)-2-methylthioacetate

To a stirred suspension of sodium hydride (6.6 g, 80% dispersion in mineral oil) in dry N,N-dimethylformamide (25 ml) under an atmosphere of nitrogen at ambient temperature was added a solution of 2-hydroxydibenzofuran (36.8 g) in N,N-dimethyl-formamide (150 ml) over 40 minutes. The mixture was stirred for 3.25 hours then a solution of ethyl 2-bromo-2-methylthioacetate (54.2 g, 90% purity) in N,N-dimethyl-formamide (50 ml) was added dropwise over 20 minutes during which time the reaction temperature was allowed to rise to 47° C. On complete addition, the mixture was stirred for 21.5 hours, poured into water and extracted with diethyl ether (three times). The extracts were combined, washed with dilute aqueous sodium hydroxide (twice), water (three times) then dried over magnesium sulfate and evaporated under reduced pressure. The residue was fractionated by chromatography (silica; diethyl ether: hexane, 1:2 to 1:1 by volume) to give an orange oil, 33 g, containing the required product that was used in the next stage without further purification. A sample of the oil was further purified by chromatography to provide an analytical sample.

$^1$H NMR (CDCl$_3$) δ ppm: 1.34-1.38 (3H,t); 2.26 (3H,s); 4.30-4.38 (2H,m); 5.64(1H,s) 7.16-7.20(1H,dd); 7.32-7.36 (1H,dd); 7.44-7.60(4H,m); 7.92-7.94(1H,d).

In a similar procedure, 7-chloro-2-hydroxydibenzofuran was reacted with ethyl 2-bromo-2-methylthioacetate to give ethyl 2-(7-chlorodibenzofuranyl-2-oxy)-2-methylthioacetate.

$^1$H NMR (CDCl$_3$) δ ppm 1.35-1.39(3H,t); 2.26(3H,s); 4.32-4.38(2H,m); 5.64(1H,s); 7.20-7.24(1H,dd); 7.40-7.54 (4H,m); 7.87(1H,d).

In a similar procedure, 2-hydroxydibenzothiophene was reacted with ethyl 2-bromo-2-methylthioacetate to give ethyl 2-(dibenzothienyl-2-oxy)-2-methylthioacetate.

$^1$H NMR (CDCl$_3$) δ ppm: 1.35-1.39 (3H,t); 2.26 (3H,s); 4.32-4.38 (2H,m); 5.72(1H,s) 7.20-7.24(1H,dd); 7.44-7.48 (3H,m); 7.78-7.80(1H,m); 7.82-7.86(1H,m); 8.08-8.12(1H, m).

Stage 3: Preparation of 2-(dibenzofuranyl-2-oxy)-2-methylthioacetic acid

To a stirred solution of ethyl 2-(dibenzofuranyl-2-oxy)-2-methylthioacetate (15.8 g) in tetrahydrofuran (250 ml) at ambient temperature was added a solution of sodium hydroxide (2.5 g) in water (25 ml). The mixture was stirred for 2 hours and evaporated under reduced pressure to remove the tetrahydrofuran. The residue was diluted with water, washed with diethyl ether (twice) and the aqueous phase acidified with concentrated hydrochloric acid then extracted with ethyl acetate (three times). The extracts were combined, washed with brine, dried over magnesium sulfate, filtered and evaporated under reduced pressure to give a yellow solid which was washed with a small volume of dichloromethane and filtered to provide 2-(dibenzofuranyl-2-oxy)-2-methylthioacetic acid, 5.90 g as a cream coloured solid, m.p. 130-132° C.

$^1$H NMR (DMSO-d$_6$) δ ppm: 2.16 (3H,s); 6.02(1H,s) 7.22-7.26(1H,dd); 7.38-7.42(1H,dd); 7.50-7.54(1H,dd); 7.64-7.70; (2H,m); 7.90(1H,m); 8.10-8.14(1H,d).

In a similar procedure, ethyl 2-(7-chlorodibenzofuranyl-2-oxy)-2-methylthioacetate was hydrolysed to give 2-(7-chlorodibenzofuranyl-2-oxy)-2-methylthioacetic acid as a pale yellow gum.

In a similar procedure, ethyl 2-(dibenzothienyl-2-oxy)-2-methylthioacetate was hydrolysed to give 2-(dibenzothienyl-2-oxy)-2-methylthioacetic acid.

$^1$H NMR (CDCl$_3$) δ ppm: 2.28 (3H,s); 5.79(1H,s); 7.11-7.15(1H,dd); 7.44-7.48(3H,m); 7.79-7.81(1H,m); 7.89-7.97 (1H,m); 8.10-8.12(1H,m).

Stage 4

Triethylamine (4.17 ml) was added to a stirred solution of 4-amino-4-methyl -pent-2-yne hydrochloride (1.95 g) in DMF (65 ml) giving a white suspension. The mixture was stirred at ambient temperature for 10 minutes then 7-aza-1-hydroxy-benzotriazole (HOAT, 2.08 g) and N-(3-dimethylaminoprgpyl)-N'-ethyl carbodiimide hydrochloride (EDC, 2.94 g) and 2-(dibenzofuranyl-2-oxy)-2-methylthioacetic acid in N,N-dimethyl-formamide (10 ml) were added. The yellow suspension was stirred at ambient temperature for 2.5 hours then stored for 18 hours. The mixture was poured into water, extracted with diethyl ether (three times) and the extracts were combined, washed with saturated aqueous sodium hydrogen carbonate, water (twice), dried over magnesium sulphate, filtered and evaporated under reduced pressure. The residual solid was washed with hexane and filtered to give the required product, 4.40 g, as a cream coloured solid, m.p. 119-120° C.

$^1$H NMR (CDCl$_3$) δ ppm: 1.70-1.72(6H, 2×s); 1.84(3H,s); 2.22(3H,s); 5.54(1H,s) 6.84(1H,s); 7.14-7.18(1H,dd); 7.34-7.38(1H,dd); 7.46-7.50(1H,dd); 7.52-7.60(3H,m); 7.90-7.94 (1H,d).

In a similar procedure, 2-(8-chlorodibenzofuranyl-2-oxy)-2-methylthioacetic acid was condensed with 4-amino-4-methyl-pent-2-yne to give 2-(8-chlorodibenzofuranyl-2-oxy)-2-methylthio-N-(2-methylpent-3-yn-2-yl)acetamide (Compound No. 4 of Table 18), yellow gum.

$^1$H NMR (CDCl$_3$) δ ppm: 1.70-1.72(6H, 2×s); 1.83(3H,s); 2.21(3H,s); 5.52(1H,s) 6.82(1H,s); 7.17-7.21(1H,dd); 7.42-7.54(4H,m); 7.89(1H,d).

In a similar procedure, 2-(dibenzothienyl-2-oxy)-2-methylthioacetic acid was condensed with 4-amino-4-methyl-pent-2-yne to give 2-(dibenzothienyl-2-oxy)-2-methylthio-N-(2-methylpent-3-yn-2-yl)acetamide (Compound No. 4 of Table 20), yellow gum.

$^1$H NMR (CDCl$_3$) δ ppm: 1.70-1.72(6H, 2×s); 1.83(3H,s); 2.21(31H,s); 5.59(1H,s) 6.82(1H,s); 7.17-7.19(1H,dd); 7.44-7.50(3H,m); 7.78(1H,m); 7.84-7.81(1H,m); 8.10-8.12(1H, m).

The following compounds were characterised by the following NMR data.

Compound No. 1 of Table 16: gum, $^1$H NMR(CH$_3$CN) δ ppm: 2.56(1H,s); 5.62(1H,s) 7.08(1H,s); 7.20(1H,dd); 7.35 (1H,dd); 7.48 (1H,dd); 7.56(2H,m); 7.70(1H,s); 7.98(1H,d).

Compound No. 5 of Table 16: gum, $^1$H NMR(CH$_3$CN) δ ppm: 5.60 (1H, s) 6.88 (1H, s); 7.20(1H,dd); 7.35(1H,dd); 7.48(1H,dd); 7.56(2H, m); 7.70(1H,s); 7.98(1H,d).

Compound No. 7 of Table 16: solid, $^1$H NMR(CH$_3$CN) δ ppm: 3.25(3H,s); 4.01(2H,s); 5.62(1H,s) 7.06(1H,s); 7.22(1H,dd); 7.36(1H,dd); 7.48(1H,dd); 7.56(2H,m); 7.70(1H,s); 7.99(1H,d).

EXAMPLE 2

This Example illustrates the preparation of 2-(indanyl-5-oxy)-2-methylthio -N-(2-methylpent-3-yn-2-yl)acetamide (Compound No. 4 of Table 2)

Stage 1: Preparation of 2-chloro-2-methylthio-N-(2-methylpent-3-yn-2-yl)acetamide Step 1

Triethylamine (1.84 ml) was added to a stirred solution of 4-amino-4-methyl -pent-2-yne hydrochloride (1.278 g) in DMF (5 ml) at ambient temperature giving a white suspension. Methylthioacetic acid (1.0 g) was dissolved in DMF (5 ml) then added to the amine followed by HOBT (1.27 g) and finally EDC (1.806 g). The white suspension was stirred at room temperature for 6 hours and stored overnight. Water was added and the aqueous phase was extracted with diethyl ether. The organic phases were combined, successively washed with water and dried over magnesium sulphate, filtered and evaporated under reduced pressure to give 2-(methylthio)-N-(2-methylpent-3-yn -2-yl)acetamide as a yellow orange solid (1.9 g).

$^1$H NMR (CDCl$_3$) δ ppm: 1.63 (6H,s); 1.82 (3H,s); 2.13 (3H,s); 3.14 (2H,s); 6.95 (1H,s).

Step 2

The product of Step 1 (0.824 g) was dissolved in carbon tetrachloride (15 ml) with warming. The solution was cooled to 0° C. and N-chlorosuccinimide (NCS, 0.653 g) was slowly added and the mixture was stirred at ambient temperature for 2 hours. The reaction mixture was filtered to remove succinimide and the resulting liquid was evaporated to give 2-(chloro)-2-(methylthio)-N-(2-methylpent-3-yn-2-yl)acetamide as a clear oil, (1.4 g), that was used without further purification.

$^1$H NMR (CDCl$_3$) δ ppm: 1.64 (6H,s); 1.82 (3H,s); 2.29 (3H,s); 5.32 (1H,s); 6.57 (1H,s).

Stage 2

To a stirred solution of 5-indanol (0.9 mM) in dry 1,4-dioxan (3 ml) was added sodium hydride (11.0 mM, 60% dispersion in mineral oil) and the mixture stirred for 30 minutes under an atmosphere of nitrogen. A solution of 2-(chloro)-2-(methylthio)-N -(2-methylpent-3-yn-2-yl)acetamide (0.68 mM) in 1,4-dioxan (2 ml) was added and the reaction stirred at ambient temperature for 18 hours then evaporated under reduced pressure. The residue was treated with water and extracted with chloroform. The extracts were combined, washed with water, dried over magnesium sulfate, evaporated under reduced pressure and fractionated by chromatography (silica; hexane:ethyl acetate 4:1 to 1:1) to give 2-(indanyl-5-oxy)-2-methylthio-N-(2-methylpent-3-yn-2-yl)acetamide as a viscous oil.

$^1$H NMR (CDCl$_3$) δ ppm: 1.68(6H, 2×s); 1.82(3H,s); 2.09 (2H,m); 2.16(3H,s); 2.88(4H,m); 5.43(1H,s); 6.79(2H,m); 6.89(1H,bs); 7.16(1H,d).

In a similar procedure, 3,4-methylenedioxyphenol was reacted with 2-(chloro)-2-(methylthio)-N-(2-methylpent-3-yn-2-yl)acetamide to give 2-(3,4-methylenedioxy-phenoxy)-2-methylthio-N-(2-methylpent-3-yn-2-yl)acetamide (Compound No. 4 of Table 3).

¹H NMR (CDCl₃) δ ppm: 1.68(6H, 2×s); 1.82(3H,s); 2.16 (3H,s); 2.88(4H,m); 5.33(1H,s); 5.96(2H,m); 6.46(1H,d); 6.60(1H,d); 6.73(1H, bs); 6.74(1H,d).

In a similar procedure, 3-phenoxyphenol was reacted with 2-chloro-2-methylthio-N-(2-methylpent-3-yn-2-yl)acetamide to give 2-(3-phenoxyphenoxy)-2-methylthio-N-(2-methylpent-3-yn-2-yl)acetamide (Compound No. 4 of Table 1).

¹H NMR (CDCl₃) δ ppm: 1.66(3H,s); 1.67(3H,s); 1.81 (3H,s); 2.15 (3H,s); 5.44 (1H,s); 6.70(4H,m); 7.04(2H,d); 7.14(1H,t); 7.27(2H,t); 7.36(2H,t).

In a similar procedure, 5-hydroxy-1,3-benzoxathiol-2-one was reacted with 2-chloro-2-methylthio-N-(2-methylpent-3-yn-2-yl)acetamide to give 5-(2-oxo-1,3-benzoxathiolyl)-2-methylthio-N-(2-methylpent-3-yn-2-yl)acetamide (Compound No. 4 of Table 7).

¹H NMR (CDCl₃) δ ppm: 1.69(6H, 2×s); 1.83(3H,s); 2.17 (3H,s); 5.46(1H,s); 6.65(1H,bs); 6.95(1H,dd); 7.03(1H,d); 7.35(1H,d).

EXAMPLE 3

This Example illustrates the preparation of 2-(3-tphenylquinolinyl-6-oxy)-2-methylthio-N-(2-methylpent-3-yn-2-yl)acetamide (Compound No. 4 of Table 22)
Stage 1: Preparation of 2-(3-bromoquinolinyl-6-oxy)-2-methylthio-N-(2-methylpent-3-yn-2-yl)acetamide
Step 1

In a similar procedure to Stage 2 of Example 1, 3-bromo-6-hydroxyquinoline (preparation described in *Liebigs Ann Chem* (1966), 98-106) was reacted with ethyl 2-bromo-2-methylthioacetate to give ethyl 2-(3-bromoquinolinyl-6-oxy)-2-methylthio-acetate as a pale yellow gum.

¹H NMR (CDCl₃) δ ppm: 1.34 (3H,t); 2.24 (3H,s); 4.30-4.38 (2H,m); 5.70 (1H,s); 7.14 (1H,m); 7.48-7.52 (1H,dd); 8.02 (1H,d); 8.22 (1H,s); 8.80 (1H,s).
Step 2

In a similar procedure to Stage 3 of Example 1, ethyl 2-(3-bromoquinolinyl-6-oxy)-2-methylthioacetate was hydrolysed to 2-(3-bromoquinolinyl-6-oxy) -2-methylthioacetic acid, colourless solid, m.p. 166-167° C.

¹H NMR (CDCl₃) δ ppm: 2.26 (3H,s); 5.76 (1H,s); 7.20 (1H,m); 7.50-7.54 (1H,dd); 8.01 (1H,d); 8.28 (1H,s); 8.78 (1H,s).
Step 3

In a similar procedure to Stage 4 of Example 1,2-(3-bromoquinolinyl-6-oxy)-2-methylthioacetic acid was condensed with 4-amino-4-methylpent-2-yne to give 2-(3-bromoquinolinyl-6-oxy)-2-methylthio-N-(2-methylpent-3-yn-2-yl)acetamide as a colourless solid, m.p. 135-137° C.

¹H NMR (CDCl₃) δ ppm: 1.70 (3H,s); 1.71 (3H,s); 1.83 (3H,s); 2.22 (3H,s); 5.62 (1H,s); 6.72 (1H,s); 7.18 (1H,d); 7.47 (1H,dd); 8.05 (1H,d); 8.24 (1H,d); 8.82 (1H,m).
Stage 2

A mixture of 2-(3-bromoquinolinyl-6-oxy)-2-methylthio-N-(2-methylpent-3-yn-2-yl)acetamide (0.200 g), tris-(dibenzylideneacetone) di-palladium (0) (0.007 g), phenyl-boronic acid (0.060 g), tri-tert.-butylphosphine tetrafluoroborate (0.006 g), cesium fluoride (0.245 g) in deoxygenated 1,4-dioxane (10 ml) were stirred at ambient temperature for 18 hours under an atmosphere of nitrogen. The mixture was filtered through kieselguhr then the filtrate was diluted with water, extracted with ethyl acetate and the organic phase separated, washed with brine, dried over magnesium sulfate and evaporated under reduced pressure to give a gum. The gum was fractionated by chromatography (silica; hexane: ethyl acetate) to give the required product, 0.028 g, as a colourless gum.

¹H NMR (CDCl₃) δ ppm: 1.69(3H,s); 1.70(3H,s); 1.82 (3H,s); 2.22(3H,s); 5.66(1H,s); 6.79(1H,s); 7.33(1H,d); 7.42-7.48(2H,m); 7.53(1H,t); 7.70(2H,d); 8.11(1H,d); 8.23(1H,d); 9.09(1H,d).

EXAMPLE 4

This Example illustrates the preparation of 2-(2-benzyloxynaphthyl-7-oxy)-2-methylthio-N-(2-methylpent-3-yn-2-yl) acetamide (Compound No. 4 of Table 24)
Stage: 1 Preparation of 2-benzyloxynaphth-7-ol A stirred solution of 2,7-dihydroxynaphthylene (4.8 g) in acetone (50 ml) containing anhydrous potassium carbonate (4.08 g) and benzyl bromide (5.13 g0 was heated to refax for 4 hours, cooled to ambient temperature then stored for 18 hours. The mixture was filtered and the filtrate evaporated under reduced pressure to give a pale green solid that was fractionated by chromatography (silica; hexane/ethyl acetate 95:5 to 1:1 by volume) to give 2-benzyloxynaphth-7-ol, 1.63 g, as a cream coloured solid, m.p. 152-154° C.
Stage 2: Preparation of ethyl 2-(2-benzyloxynaphthyl-7-oxy)-2-methylthioacetate In a similar procedure to Example 1 Stage 2,2-benzyloxynaphth-7-ol was reacted with ethyl-2-bromo-2-methylthioacetate to give ethyl 2-(2-benzyloxynaphthyl-7-oxy)-2-methylthioacetate as a pale pink oil.

¹H NMR (CDCl₃) δ ppm: 1.34 (3H,t); 2.24 (3H,s); 4.34 (2H,m); 5.18(1H,s); 5.70(1H,s); 7.10-7.14 (3H,m); 7.18 (1H, m); 7.35 (1H,d); 7.42 (2H,t); 7.46 (2H,m); 7.70(2H,t).
Stage 3: Preparation of 2-(2-benzyloxynaphthyl-7-oxy)-2-methylthioacetic acid In a similar procedure to Example 1 Stage 3, ethyl 2-(2-benzyloxynaphthyl-7-oxy)-2-methylthioacetate was hydrolysed to 2-(2-benzyloxynaphthyl-7-oxy)-2-methylthioacetic acid as a yellow gum.

¹H NMR (CDCl₃) δ ppm: 2.28 (3H,s); 5.18(2H,s); 5.78 (1H,s); 7.10-7.16 (3H,m); 7.22 (1H,d); 7.35 (1H,d); 7.46 (2H,t); 7.49 (2H,d); 7.74(2H,t).

In a similar procedure to Example 1 Stage 4, 2-(2-benzyloxynaphthyl-7-oxy)-2-methylthioacetic acid was condensed with 4-amino-4-maethyl-pent-2-yne hydrochloride to give the required product as a green gum.

¹H NMR (CDCl₃) δ ppm: 1.68(3H,s); 1.70 (3H,s); 2.20 (3H,s); 5.16(2H,s); 5.60(1H,s); 6.78(1H,bs); 7.06-7.10 (1H, dd); 7.13 (2H,m); 7.20 (1H,d); 7.35 (1H,d); 7.42 (2H,t); 7.48 (2H,d); 7.72(2H,t).

EXAMPLE 5

This Example illustrates the fungicidal properties of compounds of formula (1).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Erysiphe graminis* f. sp. *hordei* (barley powdery mildew): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity. *Erysiphe graminis* f. sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity. *Puccinia recondita* f. sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity. *Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically after 48 hours.

The following compounds (number of compound first, followed by table number in brackets) gave at least 60% control of the following fungal infection at 200 ppm:

*Plasmopara viticola*, compounds 4 (2), 4 (7), 1 (10), 4 (10), 4 (12), 4 (13), 1 (21), 4 (21), 4 (24A), 4 (24B).

*Phytophthora infestans*, compounds 4 (2), 4 (7), 1 (10), 4 (10), 4 (12), 4 (13), 4 (21), 4 (24A), 4 (24B).

*Erysiphe graminis* f. sp. *tritici*, compounds 4 (12), 1 (16), 4 (16), 7 (16).

*Pyricularia oryzae*, compounds 4 (16);

*Botrytis cinerea*, compounds 4 (1), 4 (3), 4 (16), 4 (19), 7(19), 8(19), 4 (20), 5(16), 4 (12), 4 (13).

*Erysiphe graminis* f. sp. *hordei*, compounds 1 (16), 4 (16), 7(19), 4 (20), 4 (21), 5 (16), 7 (16);

*Puccinia recondita* f. sp. *tritici*, compounds 1 (16);

*Septoria nodorum*, compounds 1 (16), 4 (16), 4 (22), 7 (16);

The following compounds (number of compound first, followed by table number in brackets) gave at least 60% control of the following fungal infection at 20 ppm:

*Pythium ultimum*, compounds 4 (2), 4 (3), 4 (7), 7 (16), 1 (10), 4 (10), 4 (13), 4 (24A), 4 (24B).

The invention claimed is:

1. A N-alkynyl-2-alkylthio-2-(aryloxy or heteroaryloxy) alkylamide of the general formula (1):

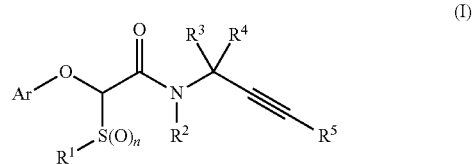

wherein
Ar is a group of the formula (B1) or (B2):

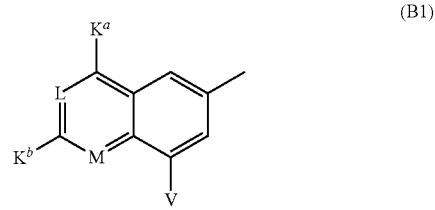

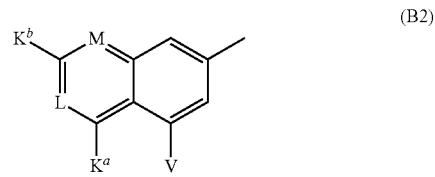

wherein L is CQ and M is N;
$K^a$ and $K^b$ are H;
V is H, or $C_{1-6}$ alkyl;
Q is phenyl or thienyl;
$R^1$ is $C_{1-4}$ alkyl;
$R^2$ is H;
$R^3$ and $R^4$ are independently $C_{1-6}$ alkyl;
$R^5$ is H or $C_{1-6}$ alkyl which is optionally substituted with $C_{1-6}$ alkoxy; and
n is 0.

2. A compound according to claim 1 wherein Ar is 3-phenylquinolin-6-yl.

3. A compound according to claim 1 wherein $R^1$ is methyl.

4. A compound according to claim 1 wherein $R^3$ and $R^4$ are both methyl.

5. A compound according to claim 1 wherein $R^5$ is H, methyl or methoxymethyl.

6. A compound according to claim 5 wherein $R^5$ is H or methyl.

7. A process for preparing a compound according to claim 1 wherein n is 0, which comprises (a) reacting the compound of the formula (4)

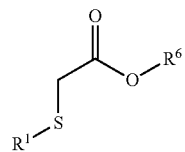
(4)

with a halogenating agent, (b) reacting the resulting compound of the formula (5)

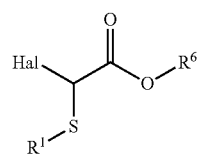
(5)

in the presence of a base with a compound Ar—OH, where R is as defined in claim 1, to yield the compound of the formula (6)

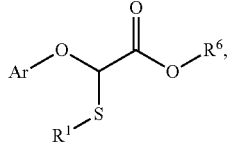
(6)

(c) converting this compound in the presence of a base to the corresponding acid of the formula (7)

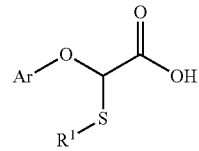
(7)

and (d) reacting this acid with an amine of the formula (8)

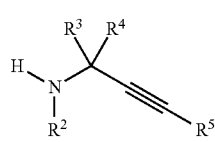
(8)

to yield the compound according to claim 1.

8. A process for preparing a compound according to claim 1 wherein n is 0, which comprises (a) reacting the compound of the formula (13)

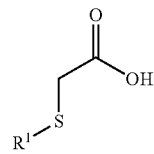
(13)

with an amine of the formula (8)

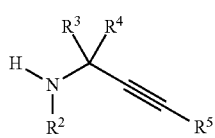
(8)

to form the compound of the formula (14)

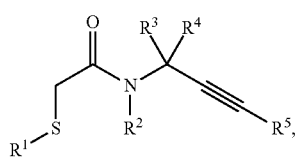
(14)

(b) treating this compound with a halogenating agent to yield the compound of the formula (16)

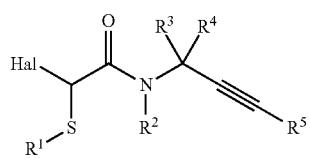
(16)

and (c) reacting this compound in the presence of a base with Ar—OH to yield the compound according to claim 1, where Ar is as defined in claim 1.

9. A fungicidal composition comprising a fungicidally effective amount of a compound of formula (1) according to claim 1 and a suitable carrier or diluent therefor.

10. A method of controlling phytopathogenic fungi which comprises applying a fungicidally effective amount of a compound of formula (1) according to claim 1 to a plant, to a seed of a plant, to the locus of the plant or seed or to soil or any other plant growth medium.

* * * * *